(12) United States Patent
Lee

(10) Patent No.: US 10,042,012 B2
(45) Date of Patent: *Aug. 7, 2018

(54) MAGNETIC RESONANCE IMAGING APPARATUS

(71) Applicant: SAMSUNG ELECTRONICS CO., LTD., Suwon-si (KR)

(72) Inventor: Myung-kyu Lee, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/368,890

(22) Filed: Dec. 5, 2016

(65) Prior Publication Data

US 2017/0082702 A1 Mar. 23, 2017

Related U.S. Application Data

(63) Continuation of application No. 14/491,148, filed on Sep. 19, 2014, now Pat. No. 9,541,613.

(30) Foreign Application Priority Data

Sep. 25, 2013 (KR) .................. 10-2013-0114139

(51) Int. Cl.
*G01V 3/00* (2006.01)
*G01R 33/28* (2006.01)
*G03B 21/14* (2006.01)
*G03B 29/00* (2006.01)
*A61B 5/055* (2006.01)
(Continued)

(52) U.S. Cl.
CPC ............ *G01R 33/283* (2013.01); *A61B 5/055* (2013.01); *G01R 33/307* (2013.01); *G01R 33/34046* (2013.01); *G01R 33/5608* (2013.01);
*G03B 21/14* (2013.01); *G03B 21/2013* (2013.01); *G03B 21/2053* (2013.01); *G03B 29/00* (2013.01)

(58) Field of Classification Search
CPC .................................................. G01R 33/283
USPC ................................................. 324/318, 322
See application file for complete search history.

(56) References Cited

U.S. PATENT DOCUMENTS 5,432,544 A 7/1995 Ziarati
6,774,929 B1 8/2004 Kopp
(Continued)

FOREIGN PATENT DOCUMENTS

CN 201920723 U 8/2011
CN 103800007 A 5/2014
(Continued)

OTHER PUBLICATIONS

International Search Report dated Jan. 8, 2015 issued by International Searching Authority in counterpart International Application No. PCT/KR2014/008843.
(Continued)

*Primary Examiner* — Louis Arana
(74) *Attorney, Agent, or Firm* — Sughrue Mion, PLLC

(57) ABSTRACT

The MRI apparatus includes a housing that includes a bore; a table which is configured to be moved into the bore; and a beam projector that is configured to be disposed on the table, and to project an image into the bore. The beam projector includes a coil which is configured to be disposed so that a central axis of the coil is parallel to a center axis of the bore.

21 Claims, 8 Drawing Sheets

(51) Int. Cl.
*G01R 33/30* (2006.01)
*G01R 33/34* (2006.01)
*G01R 33/56* (2006.01)
*G03B 21/20* (2006.01)

(56) References Cited

U.S. PATENT DOCUMENTS

| | | |
|---|---|---|
| 8,975,894 B2 | 3/2015 | Lee |
| 9,823,317 B2 | 11/2017 | Lee |
| 2005/0035253 A1 | 2/2005 | Rixom |
| 2005/0041000 A1 | 2/2005 | Plut |
| 2009/0154647 A1 | 6/2009 | Matsuzawa et al. |
| 2010/0056902 A1 | 3/2010 | Granzer et al. |
| 2012/0302868 A1 | 11/2012 | Kawashima |
| 2013/0215399 A1 | 8/2013 | Suzuki |
| 2013/0218004 A1 | 8/2013 | Yang |
| 2014/0210472 A1* | 7/2014 | Homann ............. G01R 33/36 324/309 |
| 2016/0058397 A1 | 3/2016 | Kim et al. |
| 2016/0313634 A1* | 10/2016 | Hotta ............. G03B 21/28 |
| 2017/0123021 A1* | 5/2017 | Takamori ............. G01R 33/283 |

FOREIGN PATENT DOCUMENTS

| | | |
|---|---|---|
| DE | 10 2005 018 435 A1 | 11/2005 |
| JP | 2003-190112 A | 7/2003 |
| JP | 2006-136359 A | 6/2006 |
| JP | 2009-205050 A | 9/2009 |
| JP | 2011-56121 A | 3/2011 |
| KR | 10-2013-0027656 A | 3/2013 |

OTHER PUBLICATIONS

Written Opinion dated Jan. 8, 2015 issued by International Searching Authority in counterpart International Application No. PCT/KR/2014/008843.
CSP Search Report at KIPO dated Jul. 1, 2016 issued in KR Application No. 10-2013-0144139.
Communication dated Jun. 19, 2017 by the European Patent Office in counterpart European Patent Application No. 14847222.8.
Communication dated May 28, 2018, issued by the Chinese Patent Office issued in counterpart Chinese Application No. 201480064312.7, 28 pages with translation.

* cited by examiner

MAGNETIC RESONANCE IMAGING APPARATUS

CROSS-REFERENCE TO RELATED APPLICATIONS

This is a continuation application of U.S. application Ser. No. 14/491,148 filed Sep. 19, 2014, which claims priority from Korean Patent Application No. 10-2013-0114139, filed Sep. 25, 2013, in the Korean Intellectual Property Office, the disclosures of which are incorporated herein in its entireties by reference.

BACKGROUND

1. Field

One or more exemplary embodiments relate to a magnetic resonance imaging (MRI) apparatus, and more particularly, to an MRI apparatus for displaying an image in a bore.

2. Description of the Related Art

MRI apparatuses are used for medical diagnostic imaging. MRI apparatuses include a main magnet that generates a main magnetic field, gradient coils that generate magnetic field gradients to select slices and provide positional information, and a radio frequency (RF) coil that is used to apply an electromagnetic wave to the human body for resonating an internal magnetization vector of the human body, and to receive a magnetic resonance (MR) signal. The main magnet and the coils which are used to capture an MR image are accommodated in a housing, which has a generally cylindrical structure having a bore in which a patient is placed during MR imaging.

The bore of an MRI apparatus is a small constrained space and may give the object a closed in feeling. Thus, when the capturing of the MR image is performed, there is a high possibility that the object would move due to boredom or discomfort which may result in a reduced quality of an image and the MRI would need to be re-executed. To this end, proposed is a system that provides image information to an object being imaged. As one example, proposed is a method in which an object wears glasses displaying an image, or looks at an image displayed outside of the housing by using a mirror provided in the bore. However, a method using glasses causes inconvenience to an object because the glasses displaying an image may enhance a closed in feeling, and a method using a mirror degrades a quality of a provided image.

SUMMARY

Exemplary embodiments may address at least the above problems and/or disadvantages and other disadvantages not described above. However, exemplary embodiments are not required to overcome the disadvantages described above, and may not overcome any of the problems described above.

One or more exemplary embodiments include an MRI apparatus that displays an image in a bore to mitigate inconvenience of an object caused by long-time image capturing and a narrow space in which the object is located. Furthermore, the inventor found a problem in which when a beam projector for displaying an image in a bore is disposed in the bore, noise of an audible frequency band occurs in the beam projector. Therefore, provided is an MRI apparatus for preventing the noise from occurring.

According to one or more exemplary embodiments, a magnetic resonance imaging (MRI) apparatus includes: a housing that includes a bore in which a magnetic field for capturing a magnetic resonance (MR) image is applied; a beam projector that is disposed in the bore of the housing during capture of the MR image, and projects an image onto an inner wall included in the bore of the housing; and a controller that controls the beam projector, and transfers a video signal to the beam projector, wherein, the beam projector includes at least one coil, and the beam projector is disposed such that a direction of a magnetic field, which is generated with a current applied to the at least one coil, is parallel to a direction of the magnetic field which is applied for capturing the MR image in the bore.

The magnetic field in the bore may be a main magnetic field that magnetizes an atomic nucleus of a chemical element causing an MR phenomenon.

The at least one coil may have an air-core coil structure.

The at least one coil may be a cylindrical coil, and the at least one coil may be disposed such that a central axis of the cylindrical coil is parallel to a direction of the magnetic field which is applied for capturing the MR image in the bore.

The beam projector may include: an image panel that displays an image; a light source that irradiates light onto the image panel; a light source driver that supplies certain power to the light source; and a projection lens that projects the image displayed by the image panel, and the at least one coil may be an inductor provided at the light source driver.

The light source driver may include a DC converter that converts input power into a predetermined voltage.

The light source may include red, green, and blue light sources, and the light source driver may sequentially supply a current to the red, green, and blue light sources.

The MRI apparatus may further include a moving table on which an object is located, and which enters the bore of the housing, wherein an image-forming position of the inner wall of the housing, in which the image projected from the beam projector is formed, may be moved according to a position in which the moving table enters an inside of the bore of the housing.

The beam projector may be disposed on the moving table.

The beam projector may be disposed near at least one of both ends in a length direction of the moving table.

The MRI apparatus may further include a detachable module that is disposed on the moving table, and is detachably attached to the beam projector.

A detachable module which is detachably attached to the beam projector may be disposed on the moving table. The detachable module may include first and second detachable modules which are respectively disposed near both ends in a length direction of the moving table. The detachable module may transfer power and a video signal, which are input from the controller, to the beam projector. Each of the first and second detachable modules may include a detachable sensor that detects the presence of attachment/detachment of the beam projector. The controller may supply power and the video signal to only one of the first and second detachable modules, to which the beam projector is attached, according to information about the presence of attachment/detachment of the beam projector.

The detachable module may include a projection direction changing unit that changes an image projection direction of the beam projector.

The detachable module may include an optical engine module, which projects an image, and a projection direction changing unit that changes an image projection direction of the optical engine module.

The beam projector may include a luminance sensor, and beam brightness of the beam projector may be controlled according to an internal luminance state of the bore.

The beam projector may include a driving module that provides driving force to the projection direction changing unit in order for the image projection direction of the beam projector to be changed, and the controller may control the driving module according to manipulation of a user in order for the image projection direction of the beam projector to move along a posture or looking direction of the object.

The beam projector may include a driving module, which provides driving force to the projection direction changing unit in order for the image projection direction of the beam projector to be changed, and a position tracing sensor that traces the posture or looking direction of the object. The controller may control the driving module in order for the image projection direction of the beam projector to move along the posture or looking direction of the object detected by the position tracing sensor.

The beam projector may include a luminance sensor, and beam brightness of the beam projector may be controlled according to an internal luminance state of the bore.

The projected image may include at least one of an MR image being captured, imaging information, and video content.

The inner wall of the housing may include a cylindrically curved surface.

The cylindrical structure may denote a case, in which the bore of the housing is wholly cylindrical, or a case in which the bore of the housing is partially cylindrical. Alternatively, at least one surface of the inner wall of the housing may be flat, and the beam projector may project an image onto the at least one flat surface.

The MRI apparatus may include a correction processing unit that causes first distortion in an image to be projected by the beam projector, and processes a signal of the image to be projected by the beam projector so as to counteract second distortion of an image to be generated according to a curved shape of the inner wall of the housing or askew image projection. The second distortion may be curved-surface distortion caused by the curved shape of the inner wall of the housing or skew distortion caused by askew projection. The first distortion may be pre-distortion because the first distortion is previously caused to counteract the curved-surface distortion or the skew distortion. The correction processing unit may change a distortion amount of the first distortion according to the image projection direction of the beam projector being changed.

The beam projector may further include a heat dissipating module that dissipates generated heat. The heat dissipating module may be a heat sink of a nonmagnetic material.

According to one or more exemplary embodiments, a method of displaying an image in a bore of a magnetic resonance imaging (MRI) apparatus includes: entering a moving table, on which an object is located, into a bore of a housing in which a magnetic field for capturing a magnetic resonance (MR) image is applied; disposing a beam projector in the bore of the housing; and projecting an image onto an inner wall included in the bore of the housing, wherein, the beam projector includes at least one coil, and the disposing of a beam projector includes disposing the beam projector such that a direction of a magnetic field, which is generated with a current applied to the at least one coil, is parallel to a direction of the magnetic field which is applied for capturing the MR image in the bore.

The method may further include causing first distortion in an image to be projected by the beam projector, and counteracting second distortion of an image to be generated according to a curved shape of the inner wall of the housing or askew image projection.

The method may further include: changing an image projection direction of the beam projector which is projected onto the inner wall of the housing; and changing a distortion amount of the first distortion according to the image projection direction being changed.

In the projecting of an image, the image may start to be projected at a timing when the moving table enters the inside of the bore of the housing, or when a head of an object enters the inside of the bore of the housing.

A first arrangement, in which the head of the object faces a direction in which the moving table enters the inside of the bore of the housing, and a second arrangement, in which legs of the object face the direction in which the moving table enters the inside of the bore of the housing, have different timings when the beam projector starts to project an image. For example, in the first arrangement, the beam projector may start to project the image onto the inner wall of the housing at a timing when the head of the object enters the inside of the bore of the housing, and in the second arrangement, the beam projector may start to project the image onto the inner wall of the housing at a timing when a neck of the object enters the inside of the bore of the housing.

The method may further include changing the image projection direction of the beam projector according to a posture or looking direction of an object onto which an image is to be projected.

The beam projector may include an luminance sensor, and beam brightness of the beam projector may be controlled according to an internal luminance state of the bore.

The disposing of a beam projector may include disposing the beam projector on the moving table, wherein an image may be displayed in the bore of the MRI apparatus, in which the beam projector is disposed in the bore of the housing, when the moving table enters an inside of the bore of the housing.

BRIEF DESCRIPTION OF THE DRAWINGS

The above and/or other aspects will become more apparent by describing in detail certain exemplary embodiments, with reference to the accompanying drawings, in which.

DETAILED DESCRIPTION

Figure 1:
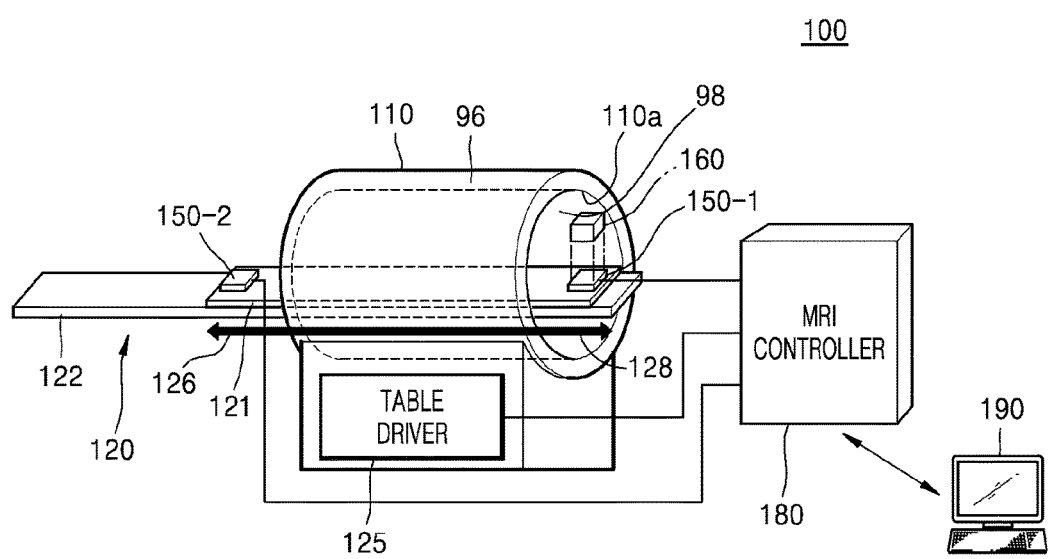
FIG. 1 illustrates a schematic configuration of an MRI apparatus according to an exemplary embodiment.

Certain exemplary embodiments are described in greater detail below with reference to the accompanying drawings.

In the following description, same reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, functions or elements known in the related art are not described in detail since they would obscure the exemplary embodiments with unnecessary detail.

In the description, when a part "includes" or "comprises" an element, unless there is a particular description contrary thereto, the part can further include other elements, not excluding the other elements. Also, the term 'unit' in the exemplary embodiments means a software component or hardware components such as a field-programmable gate array (FPGA) or an application-specific integrated circuit (ASIC), and performs a specific function. However, the term 'unit' is not limited to software or hardware. The 'unit' may be formed so as to be in a addressable storage medium, or may be formed so as to operate one or more processors. Thus, for example, the term 'unit' may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and 'units' may be associated with the smaller number of components and 'units', or may be divided into additional components and 'units'.

Throughout the specification, a "user" may be, but is not limited to, a medical expert including a doctor, a nurse, a medical laboratory technologist, a medial image expert, and a technician who repairs a medical apparatus.

Figure 2:
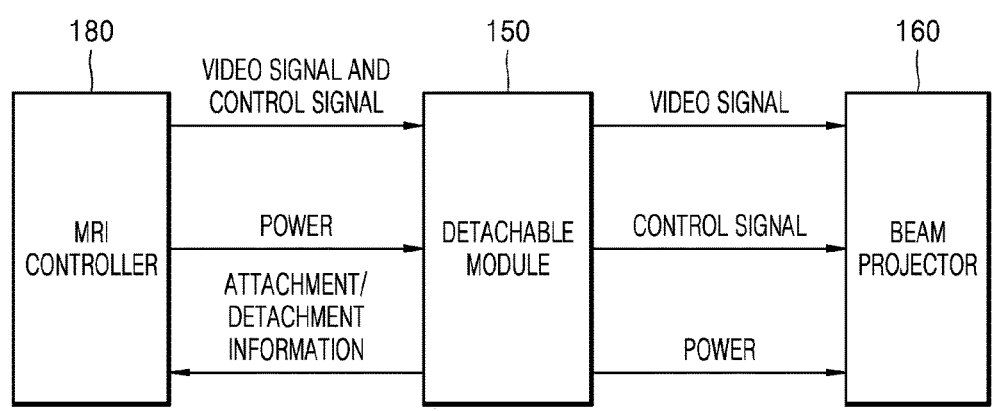
FIG. 2 illustrates a block diagram of a display apparatus in a bore of the MRI apparatus of FIG. 1.
Figure 3:
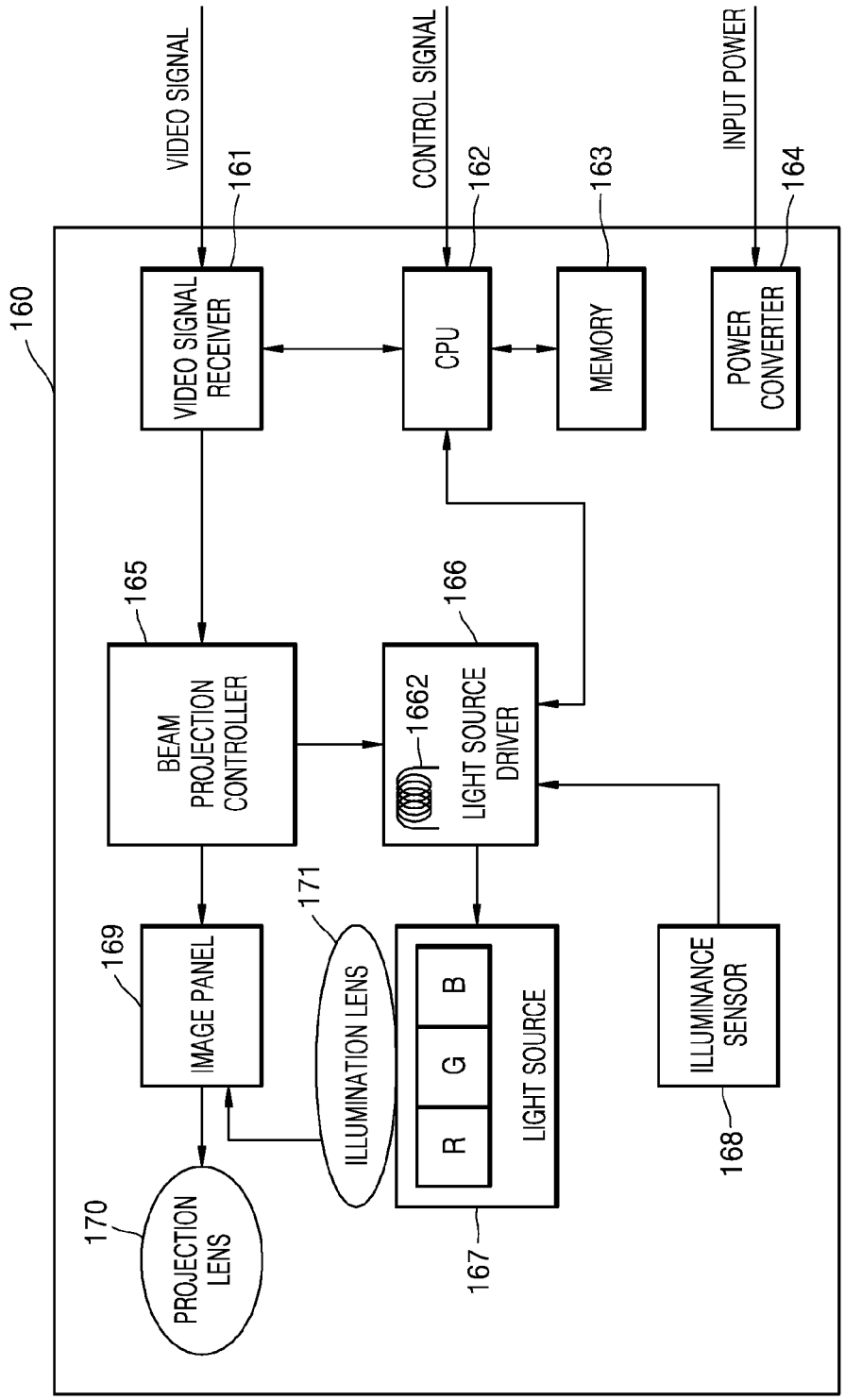
FIG. 3 illustrates a block diagram of a beam projector of the MRI apparatus of FIG. 1.
Figure 4:
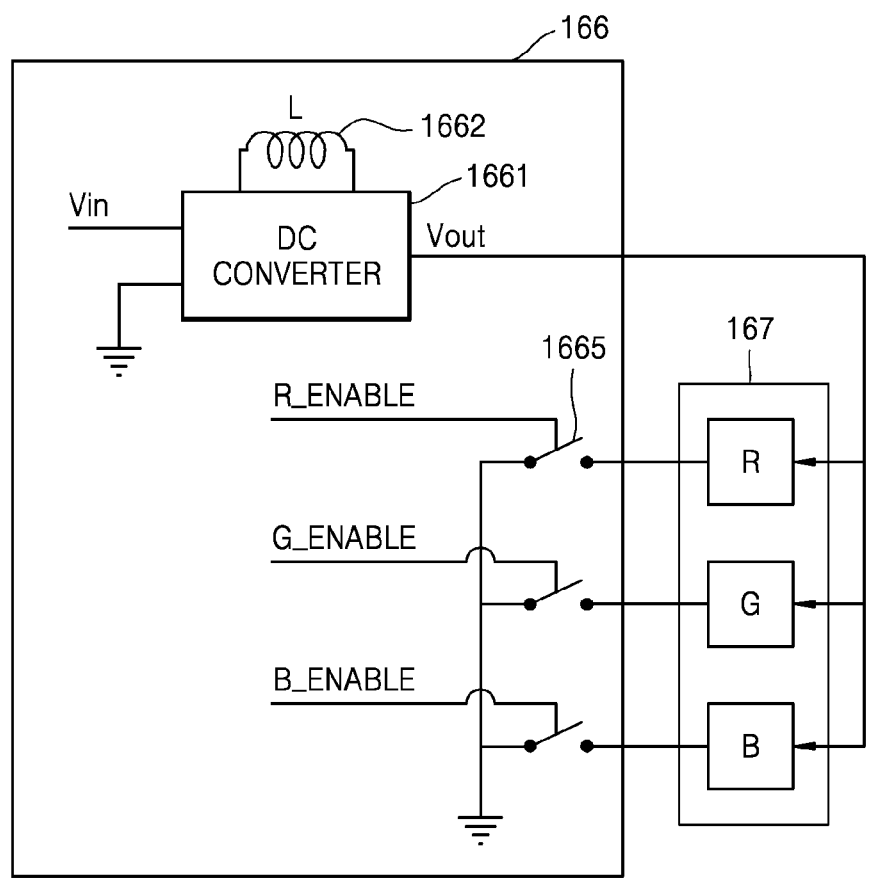
FIG. 4 illustrates an example of a driving circuit of a light source driver in the beam projector of FIG. 3.

FIG. 1 illustrates a schematic configuration of an MRI apparatus 100 according to an exemplary embodiment, and FIG. 2 illustrates a block diagram of a display apparatus in a bore of the MRI apparatus 100 of FIG. 1. FIG. 3 illustrates a block diagram of a beam projector 160 of the MRI apparatus 100 of FIG. 1, and FIG. 4 illustrates an example of a driving circuit of a light source driver in the beam projector 160 of FIG. 3.

Referring to FIGS. 1 and 2, the MRI apparatus 100 according to the present exemplary embodiment includes a magnetic assembly 96 disposed in a housing 110, which applies a magnetic field for an MR image to the inside of a housing 110, and an MRI controller 180 that applies power to the magnetic assembly and controls the magnetic assembly. The MRI apparatus 100 enables a user to manipulate the MRI controller 180 by using a console 190 which is provided outside the MRI apparatus 100, and the console 190 displays an image generated by the MRI apparatus 100.

The housing 110 has a cylindrical structure including a bore 98, and a table 120 with an object located thereon is moved into the bore. Here, the cylindrical structure denotes a case, in which the bore of the housing 110 is wholly cylindrical, or a case in which the bore of the housing 110 is partially cylindrical. Reference numeral 110a refers to an inner wall 110a configuring the bore of the housing 110. As described below, the inner wall 110a of the housing 110 acts as a screen for the beam projector 160.

The magnetic assembly is accommodated in the housing 110 having a cylindrical structure, and includes a main magnet and a gradient coil. The main magnet generates a main magnetic field ($B_0$ of FIG. 5) that magnetizes a chemical element (i.e., an atomic nucleus such as hydrogen, phosphorous, or natrium) causing an MR phenomenon among chemical elements distributed in a human body. The main magnet may be a superconductive magnet or a permanent magnet. For example, the superconductive magnet may be used to generate a magnetic field of 0.5 T or more. The main magnet may be provided to have a cylindrical structure corresponding to the cylindrical structure of the housing 110, and the main magnetic field $B_0$ generated by the main magnet may have a direction parallel to a center axis of the bore. The gradient coil generates a spatially linear gradient magnetic field for capturing an MR image. Generally, three gradient coils which respectively generate gradient magnetic fields in an x-direction, a y-direction, and a z-direction are used for an MR image. When a magnetization vector is rotating on a horizontal plane, the gradient coil spatially controls a rotation frequency or a phase of the magnetization vector in order for an MR image signal to be expressed in a spatial frequency domain, namely, a k-domain. The MRI apparatus 100 according to the present exemplary embodiment includes an RF coil that is used to apply an electromagnetic wave to a human body for resonating an internal magnetization vector of the human body, and to receive an MR signal. The RF coil may be provided at an inner surface of the gradient coil, and may configure a portion of a cylindrical magnetic structure along with the main magnet and the gradient coil. Alternatively, the RF coil may be provided as a separate module in the bore of the housing 110. The magnetic assembly for generating an MR image is known to one of ordinary skill in the art.

The table 120 includes a moving table 121 that moves to inside the housing 110 in a state where an object lies on the table 120, a support 122 that supports the moving table 121, and a table driver 125 that drives the moving table 121 in a direction of an arrow 126 or 128 according to control by the MRI controller 180.

A display apparatus provided in the bore is configured with the beam projector 160 that projects an image onto the bore of the housing 110, and at least one of a first detachable module 150-1 and a second detachable module 150-2 that is detachably attached to the beam projector 160. The MRI controller 180 controls the beam projector 160, the first detachable module 150-1 and the second detachable module 150-2.

The first detachable module 150-1 and the second detachable module 150-2 are provided on the moving table 121, and the beam projector 160 is detachably attached thereto. A coupling part between the first and second detachable modules 150-1, 150-2 and the beam projector 160 may use a connector or a docking method which is known to one of ordinary skill in the art.

One of the first detachable module 150-1 and the second detachable module 150-2 may be disposed adjacent to a position at which a head of an object lying for imaging is located. The head position of the object may be changed according to an imaging purpose. Thus, the first and second detachable modules 150-1 and 150-2 may be respectively disposed at positions adjacent to both ends in a length direction of the moving table 121. The first and second detachable modules 150-1 and 150-2 may include the same elements. The beam projector 160 may be detachably attached to each of the first and second detachable modules 150-1 and 150-2. In addition, each of the first and second detachable modules 150-1 and 150-2 may act as a connector that transfers power, a video signal, and a control signal (which are supplied from the MRI controller 180 provided outside the housing 110) to the beam projector 160. Furthermore, each of the first and second detachable modules 150-1 and 150-2 may include a detachable sensor (not shown) for detecting attachment/detachment of the beam projector 160, and transfer information, for example, attachment/detachment information, about the presence of attachment of the beam projector 160 to the MRI controller 180.

The MRI controller 180 processes the control signal, which controls the first detachable module 150-1, the second detachable module 150-2 and the beam projector 160, and the video signal supplied to the beam projector 160. Also, the MRI controller 180 may control various elements of the MRI apparatus 100, and process an MR image. As described below, the video signal supplied to the beam projector 160 may be relevant to various contents that mitigate a tension of an object during an imaging time and provide useful information. The contents may include, for example, a moving image, a photograph, imaging state information (imaging time information, imaging guide information, and imaging part information), and function MRI (FRMI) information. When the detachable sensor for detecting attachment/detachment of the beam projector 160 is provided at each of the first and second detachable modules 150-1 and 150-2, the MRI controller 180 may selectively supply the video signal, the control signal, and projector power to one of the first and second detachable modules 150-1 and 150-2 to which the beam projector is attached.

The beam projector 160 is an element that projects an image. The beam projector 160 may be selectively attached (i.e., docked) to one of the first and second detachable modules 150-1 and 150-2. When the moving table 121 is inserted into the bore of the housing 110 with the beam projector 160 being attached to one of the first and second detachable modules 150-1 and 150-2, the beam projector 160 projects an optical beam of an image onto the inner wall 110a configuring the bore. That is, the inner wall 110a of the housing 110 acts as a screen for the beam projector 160.

FIG. 3 illustrates a block diagram of the beam projector 160. Referring to FIGS. 2 and 3, the beam projector 160 includes a video signal receiver 161, a central processing unit (CPU) 162, a beam projection controller 165, a light source driver 166, a light source 167, an image panel 169, a projection lens 170, and an illumination lens 171. When the video signal transferred from the MRI controller 180 is input, the video signal receiver 161 transfers the video signal to the beam projection controller 165. The transferred video signal is converted into an image signal for beam projection by the beam projection controller 165, and the image signal is transferred to the image panel 169. The image panel 169 may use, for example, a known image panel such as a transmissive liquid crystal display (LCD) panel, a reflective DMD panel, or the like. The beam projection controller 165 transfers a light source driving signal corresponding to the image signal for beam projection to the light source driver 166. The CPU 162 that controls the video signal receiver 161 or the light source driver 166 may be provided with the control signal input to the beam projector 160 and control data stored in a memory 163. Also, a power converter 164 that converts power to a level suitable for various elements of the beam projector 160 may be built into the beam projector 160. The image panel 169 displays an image according to the image signal for beam projection, and when the light source 167 is driven according to the transferred light source driving signal, an optical beam irradiated on the image panel 169 through the illumination lens 171 passes through the image panel 169 or is reflected by the image panel 169, and thus is modulated according to an image displayed by the image panel 169 and is projected through the projection lens 170. The light source 167 may use, for example, a light emitting diode (LED), a lamp, or any other appropriate light source.

The projection lens 170 automatically or manually controls a focus in order for an optical beam of a projected image to be image-formed at an inner wall of the housing 110.

In order to display the projected image in color, for example, the light source 167 may include a red (R) light source, a green (G) light source, and a blue (B) light source, which may be sequentially driven. The MRI controller 180 supplies the video signal corresponding to a color image. The beam projection controller 165 decomposes the color image corresponding to one frame into a red image, a green image, and a blue image, and sequentially transfers the red image, the green image, and the blue image to the image panel 169 in synchronization with sequential driving of the red light source, green light source, and blue light source of the light source 167. Therefore, an image projected by the beam projector 160 may be displayed in color. The light source 167 may include a single-color light source in addition to the red light source, the green light source, and the blue light source.

The beam projector 160 may further include a luminance sensor 168 that senses an internal luminance of the bore of the housing 110. The internal luminance information of the bore sensed by the luminance sensor 168 may be transferred to the light source driver 166, and may be used to adjust brightness in driving the light source 167. Also, brightness may be changed according to a depth of the bore of the housing 110. Therefore, in response to a depth to which the moving table 121 moves into the housing 110, brightness of the light source 167 may be controlled to be suitable for the depth. That is, as a position of an image formed at the inner wall 110a of the housing 110 is moved, a light amount of an image projected onto the beam projector 160 is changed, and thus, the projected image maintains constant brightness.

Since heat is generated by the light source 167 while the beam projector 160 is being driven, an object is sensitive to the heat generated from the beam projector 160. Therefore, the beam projector 160 is disposed to be separated from a head of the object by a certain gap. The beam projector 160 may further include a heat dissipating member (not shown). The heat dissipating member may use a known element such as a heat sink, a heat dissipating fan, or the like. When an electromagnetic motor is used for driving the heat dissipating fan, an electromagnetic shield may be used in consideration of an internal high magnetic field of the bore of the housing 110.

Since an image for projection has various resolutions and a screen size, the beam projection controller 165 may perform scaling signal processing that converts the input video signal so as to match a format (for example, a resolution, a screen size, etc.) for beam projection. When a user manipulates the console 190 to select an image to be projected, an image output change request is transferred to the beam projector 160 through the MRI controller 180, and the beam projection controller 165 may operate according to the image output change request. Such a scaler may be provided in the MRI controller 180.

The beam projector 160 is inserted into the bore of the housing 110 along with the moving table 121, and thus may include an electromagnetic shield such that an internal magnetic field and electric field of the bore of the housing 110 is not affected by the beam projector 160 or does not affect the beam projector 160.

Moreover, the beam projector 160 may have a circuit configuration that minimizes an influence of the internal high magnetic field of the bore in the housing 110.

The inventor found a problem in which when the beam projector 160 is disposed in the bore of the MRI apparatus 100, noise of an audible frequency band occurs. Therefore, the inventor found that the noise of the audible frequency band is removed by adjusting a coil among the elements of the beam projector 160 such that a direction of a magnetic field, which is generated by the coil according to a current being applied to the coil, is parallel to a direction of the main magnetic field ($B_0$ of FIG. 5) which is applied for capturing an MR image in the bore.

The coil, for example, may be applied to the light source driver 166 of the beam projector 160. Hereinafter, a case in which the coil is applied to the light source driver 166 will be described as an example.

FIG. 4 illustrates a portion of a driving circuit in the light source driver 166 which is a portion of a circuit block of the beam projector 160.

The light source driver 166 may increase or decrease a voltage supplied to the beam projector 160. Also, a power source for a light source supplies a constant voltage even when a current is rapidly changed, for maintaining constant brightness of the light source 167 when the beam projector 160 operates. In the following description of the light source driver 166, an LED is used as the light source 167 as an example.

Referring to FIG. 4, the light source driver 166 according to the present exemplary embodiment may include a direct current (DC) converter 1661. The DC converter 1661 may be a DC-DC converter that converts an input DC voltage into a predetermined voltage. Voltage conversion by the DC converter 1661 may be performed, for example, by adjusting a ratio of an on time and an off time through pulse width modulation. In the voltage conversion, a current flowing in a circuit is rapidly changed each time switching between on and off is performed. Therefore, the DC converter 1661 may use a coil type inductor 1662 for responding to a fast switching operation.

The inductor 1662 may have a cylindrical air-core coil structure. A cylindrical air-core coil has a structure in which a wire is wound in a cylindrical shape of which the inside is empty or is supported by a nonmagnetic material (for example, Bakelite). A magnetic core, such as iron or ferrite which is directly provided with magnetic force from a magnetic field, is not applied to the inductor 1662, thereby minimizing an influence of a stronger magnetic field generated in the bore of the housing 110.

Figure 5:
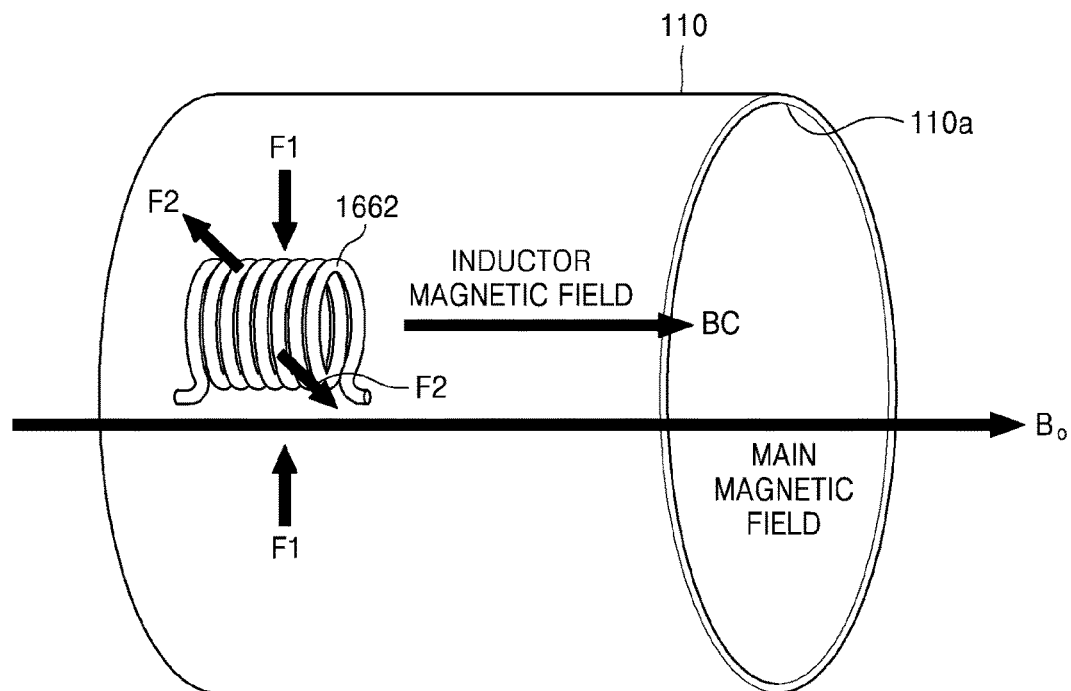
FIG. 5 is a diagram for describing a relationship between a magnetic field in the bore and a coil arrangement of the beam projector in the MRI apparatus of FIG. 1.

Moreover, as illustrated in FIG. 5, a cylindrical coil configuring the inductor 1662 is disposed such that a central axis of the cylindrical coil is parallel to a direction of the main magnetic field $B_0$ generated by the main magnet of the MRI apparatus 100. When a current is applied to the cylindrical coil, a magnetic field is generated inside the cylindrical coil in a direction parallel to the central axis of the cylindrical coil. Therefore, as illustrated in FIG. 5, the cylindrical coil configuring the inductor 1662 is disposed such that the central axis of the cylindrical coil is parallel to the direction of the main magnetic field $B_0$, and thus, a direction of a magnetic field (hereinafter referred to as an inductor magnetic field) generated when a current flows in the coil itself of the inductor 1662 may be parallel to the direction of the main magnetic field $B_0$. As described above, the main magnetic field $B_0$ generated by the main magnet may have a direction parallel to the center axis of the bore of the housing 110, and thus, the center axis of the inductor 1662 may have a direction parallel to the center axis of the housing 110.

Figure 6:
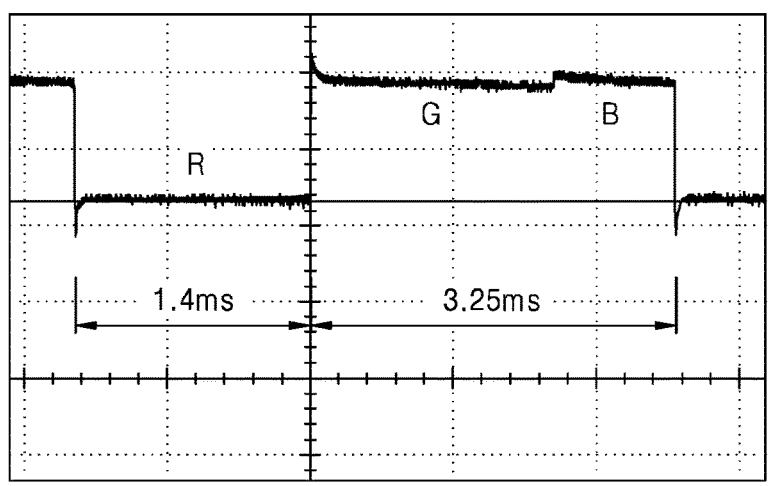
FIG. 6 shows an example in which the light source driver of FIG. 4 applies power to R, G, and B light sources.

Next, an operation of the light source driver 166 and an influence of the main magnetic field $B_0$ generated by the main magnet will be described in detail with reference to FIGS. 4 to 6.

Referring to FIG. 4, power output from the DC converter 1661 is supplied to the red light source, green light source, and blue light source of the light source 167. The light source driver 166 respectively applies red, green, and blue enable signals R_ENABLE, G_ENABLE and B_ENABLE to a plurality of switching elements 1665 (which are respectively connected to the red light source, green light source, and blue light source of the light source 167) according to a light source driving signal transferred from the beam projection controller 165. Thus, the red light source, green light source, and blue light source of the light source 167 may be sequentially driven. FIG. 6 shows examples of driving signals respectively applied to the red light source, the green light source, and the blue light source. As shown in FIG. 6, for example, a driving signal for the red light source is a pulse wave of 1.4 ms, which corresponds to an audible frequency band of 833 Hz. A driving current for the green and blue light sources is a pulse wave of 3.25 ms, which corresponds to an audible frequency band of 397.7 Hz.

As described above, when the beam projector 160 is located in the bore, the inductor 1662 of the beam projector 160 may be provided with force obtained by an electromagnetic interaction with the main magnetic field $B_0$ generated in the bore. That is, when the driving current supplied to the red light source, green light source, and blue light source of the light source 167 flows in a circuit of the light source driver 166, force is applied to a wire configuring the coil of the inductor 1662 according to Fleming's left-hand rule. Here, the force is periodically applied to the wire at the above-described audible frequency band.

If the central axis of the cylindrical coil configuring the inductor 1662 is inclined with respect to the direction of the main magnetic field $B_0$ generated by the main magnet, force acting on the wire configuring the coil of the inductor 1662 acts like F2 illustrated in FIG. 5, and thus, a balance of force is broken, causing the inductor 1662 having the cylindrical coil type to vibrate (i.e., noise) at the audible frequency band. Introduction of the beam projector 160 provides various contents (for example, a moving image, a photograph, imaging state information (imaging time information, imaging guide information, and imaging part information), and FRMI information) to an object for whom an MR image is being captured, thereby giving the object a psychologically stable feeling. However, when noise of the audible frequency band occurs, an adverse effect is applied to an examination environment of the object.

In the MRI apparatus 100 according to the present exemplary embodiment, as described above, the arrangement direction of the inductor 1662 is set such that the direction of the inductor magnetic field, which is generated with a current flowing in the inductor 1662, is parallel to the direction of the main magnetic field $B_0$ generated by the main magnet, namely, the central axis of the cylindrical coil configuring the inductor 1662 is disposed to be parallel to the direction of the main magnetic $B_0$ generated by the main magnet, and thus, force acting on the wire configuring the coil of the inductor 1662 symmetrically acts like F1 illustrated in FIG. 5 to counteract vibration. Accordingly, the MRI apparatus 100 according to the present exemplary embodiment provides various contents to an object in a state where noise does not occur in the beam projector 160.

In the present exemplary embodiment, the detailed configuration of the light source driver 166 is only an example, but is not limited thereto. Since various driving circuits using a coil are known, as described above, the coil applied to the various driving circuits is also disposed such that a magnetic field, which is generated by the coil when a current is applied to the coil, is parallel to the direction of the main magnetic field in the bore, thereby preventing noise from occurring in the coil.

Moreover, in the present exemplary embodiment, the inductor 1662 of the light source driver 166 is described as an example of the coil applied to the beam projector 160, but is not limited thereto. A coil may be applied to the other element of the beam projector 160, in addition to the light source driver 166. For example, a coil may be applied to the power converter 164 among the elements of the beam projector 160. In this case, as described above, the coil may be disposed such that a magnetic field, which is generated by the coil when a current is applied to the coil, is parallel to the direction of the main magnetic field in the bore, thereby preventing noise from occurring in the coil.

Next, an operation of the MRI apparatus 100 according to an exemplary embodiment will be described in detail with reference to FIGS. 7 to 9.

Figure 7:
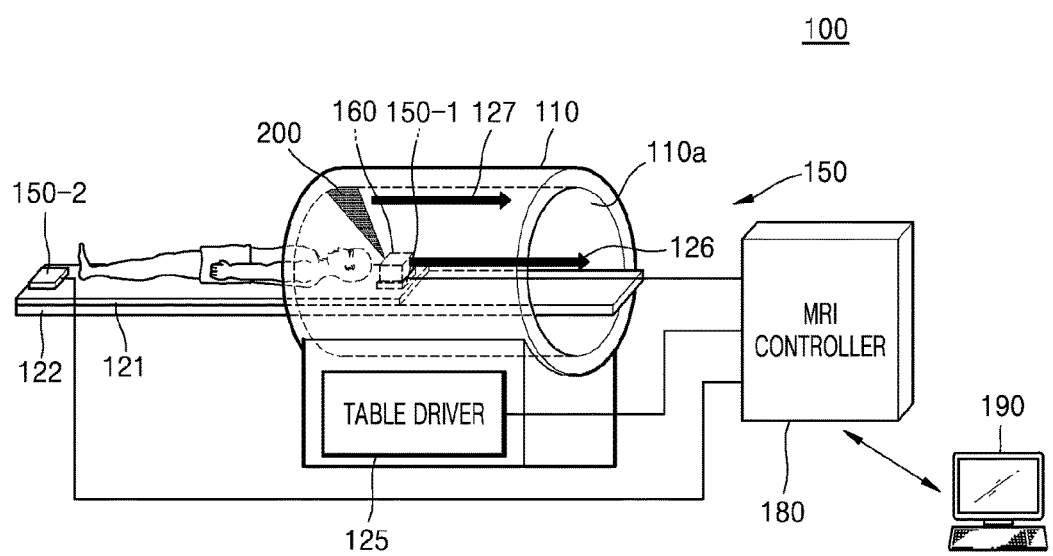
FIGS. 7, 8, and 9 illustrate an operation of the MRI apparatus of FIG. 1.
Figure 8:
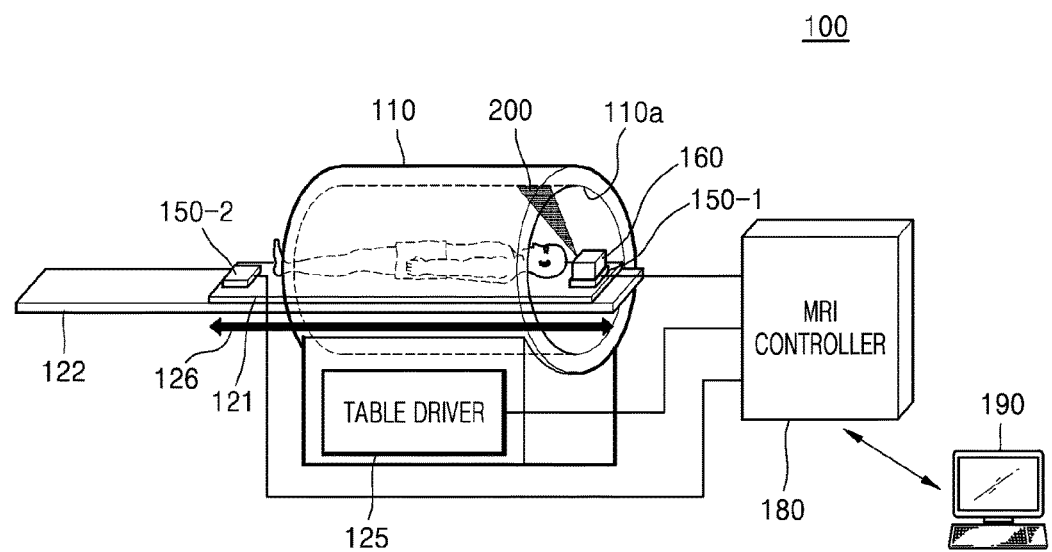
Figure 9:
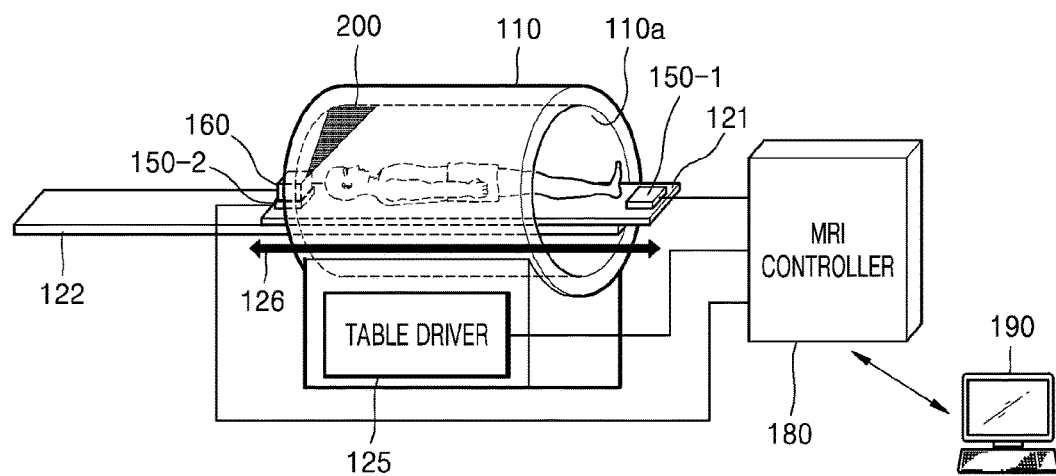

FIGS. 7 and 8 illustrate an operation in which with an object lying on the moving table 121, the object is moved (direction arrow 126) in the bore of the housing 110. Referring to FIGS. 7 and 8, capturing of an MR image is performed with the object lying on the moving table 121. Therefore, before the MR image starts to be captured, the beam projector 160 is mounted on one of the first and second detachable modules 150-1 and 150-2 which is adjacent to a head of the object. FIGS. 7 and 8 exemplarily illustrate a case in which the first detachable module 150-1 is adjacent to the head of the object.

When the MR image starts to be captured, the moving table 121 enters the inside of the bore of the housing 110. When the moving table 121 enters the inside of the bore of the housing 110, the beam projector 160 is driven to project an image onto the inner wall 110a of the housing 110. A timing when the beam projector 160 starts to project the image may be a timing, when the head of the object enters the bore of the housing 110, or a timing immediately before or after the timing. Alternatively, the timing when the beam projector 160 starts to project the image may be set to a timing when the moving table 121 enters the inside of the bore of the housing 110, regardless of a head position of the object.

The beam projector 160 projects an image onto the inner wall 110a of the housing 110 which is disposed at a position facing eyes of the object. When it is requested that the eyes of the object are fixed to a state of looking at an upper side while capturing an image, the beam projector 160 may projector an image onto the inner wall 110a of the housing 110 which is disposed over the head of the object.

When the beam projector 160 is disposed adjacent to the head of the object, an image of the beam projector may be projected with a viewing angle of the object being ensured. Also, when the beam projector 160 is disposed on the moving table 121, the moving table 121 is moved (direction arrow 126), and simultaneously the image 200 projected by the beam projector 160 is also moved (direction arrow 127). Therefore, the image is moved along with the movement of the moving table 121 while an image of the object is being captured, and thus, the object looks at the image without moving the eyes.

A projected image may be, for example, content such as a moving image, a photograph, imaging state information (imaging time information, imaging guide information, and imaging part information), or FRMI information). For example, when an MR image starts to be captured, schematic imaging guide information may be displayed. Also, an imaging end time may be displayed in real time. In addition, an image including content such as a news irrelevant to imaging may be displayed for mitigating a tension of the object.

A direction facing the head of the object may be reversely changed with respect to a length direction of the moving table 120 according to an imaging purpose. Referring to FIG. 9, the direction facing the head of the object is opposite to a direction illustrated in FIGS. 7 and 8. When a position of the object is reversely changed, the beam projector 160 is detached from the first detachable module 150-1, and is attached to the second detachable module 150-2 adjacent to the head of the object of which a lying position has been reversely changed. That is, in FIGS. 7 and 8, since the head of the object is disposed adjacent to the first detachable module 150-1, the beam projector 160 operates in a state of being attached to the first detachable module 150-1. On the other hand, in FIG. 9, since the head of the object is changed to be adjacent to the second detachable module 150-2, the beam projector 160 is detached from the first detachable module 150-1, and is attached to the second detachable module 150-2. As described above, the detachable sensor is included in each of the first and second detachable modules 150-1 and 150-2, and detects attachment/detachment. When information about attachment/detachment of the beam projector 160 is transferred, the MRI controller 180 stops the supply of the video signal and/or control signal and power to the first detachable module 150-1 from which the beam projector 160 is detached, and starts the supply of the video signal and/or control signal and power to the second detachable module 150-2 from which the beam projector 160 is attached detached.

A first arrangement (see FIGS. 7 and 8), in which the head of the object faces a direction in which the moving table 121 enters the inside of the bore of the housing 110, and a second arrangement (see FIG. 9), in which legs of the object face the direction in which the moving table 121 enters the inside of the bore of the housing 110, have different timings when the beam projector 160 starts to project an image. That is, in the first arrangement, the beam projector 160 starts to project the image onto the inner wall 110a of the housing 110 at a timing when the head of the object enters the inside of the bore of the housing 110, and in the second arrangement, the beam projector 160 starts to project the image onto the inner wall 110a of the housing 110 at a timing when a neck of the object enters the inside of the bore of the housing 110. However, a timing when the beam projector 160 projects the image may be changed by selection of the user.

When the user selects appropriate content by using the console 190, information of the selected content is transferred to the beam projector 160 through the MRI controller 180 and at least one of the first and second detachable modules 150-1, 150-2, and the CPU 162 which receives a request for an image output of the beam projector 160 controls the elements of the beam projector 160 in order for the beam projector 160 to project the image. When the selected content does not match a resolution and a screen size which are appropriate for image output, the MRI controller 180 may transfer a control command requiring the changing of image output to the beam projector 160, and the beam projection controller 165 of the beam projector 160 may perform down/up scaling of the selected content so as to match the resolution and the screen size, which are appropriate for image output, according to the image output change request.

As described above, since the MRI apparatus 100 according to an exemplary embodiment displays an image in an internal space of the bore in a beam projection scheme to provide various contents to an object, the MRI apparatus 100 mitigates boredom or inconvenience of the object caused by long-time imaging, and thus decreases a movement of the object, thereby preventing a quality of a captured image from being degraded.

Figure 10:
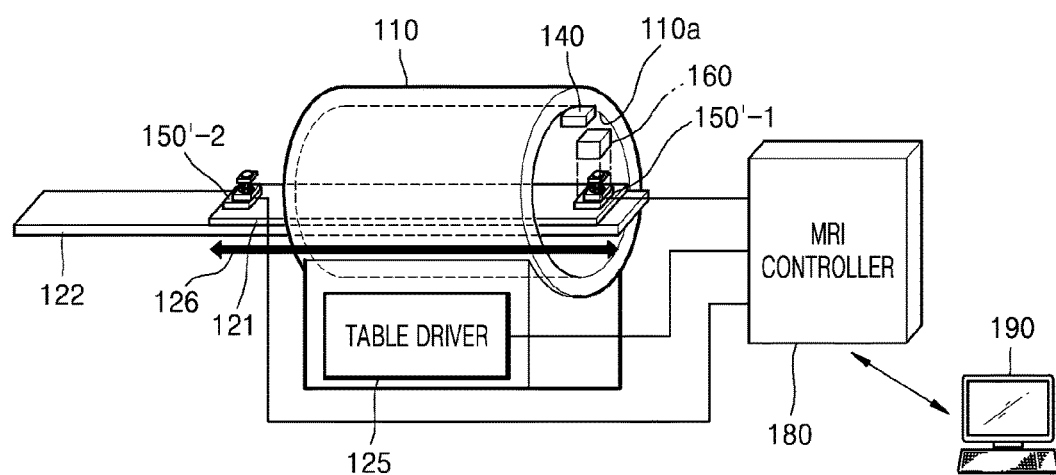
FIG. 10 illustrates a schematic configuration of an MRI apparatus according to another exemplary embodiment.
Figure 11:
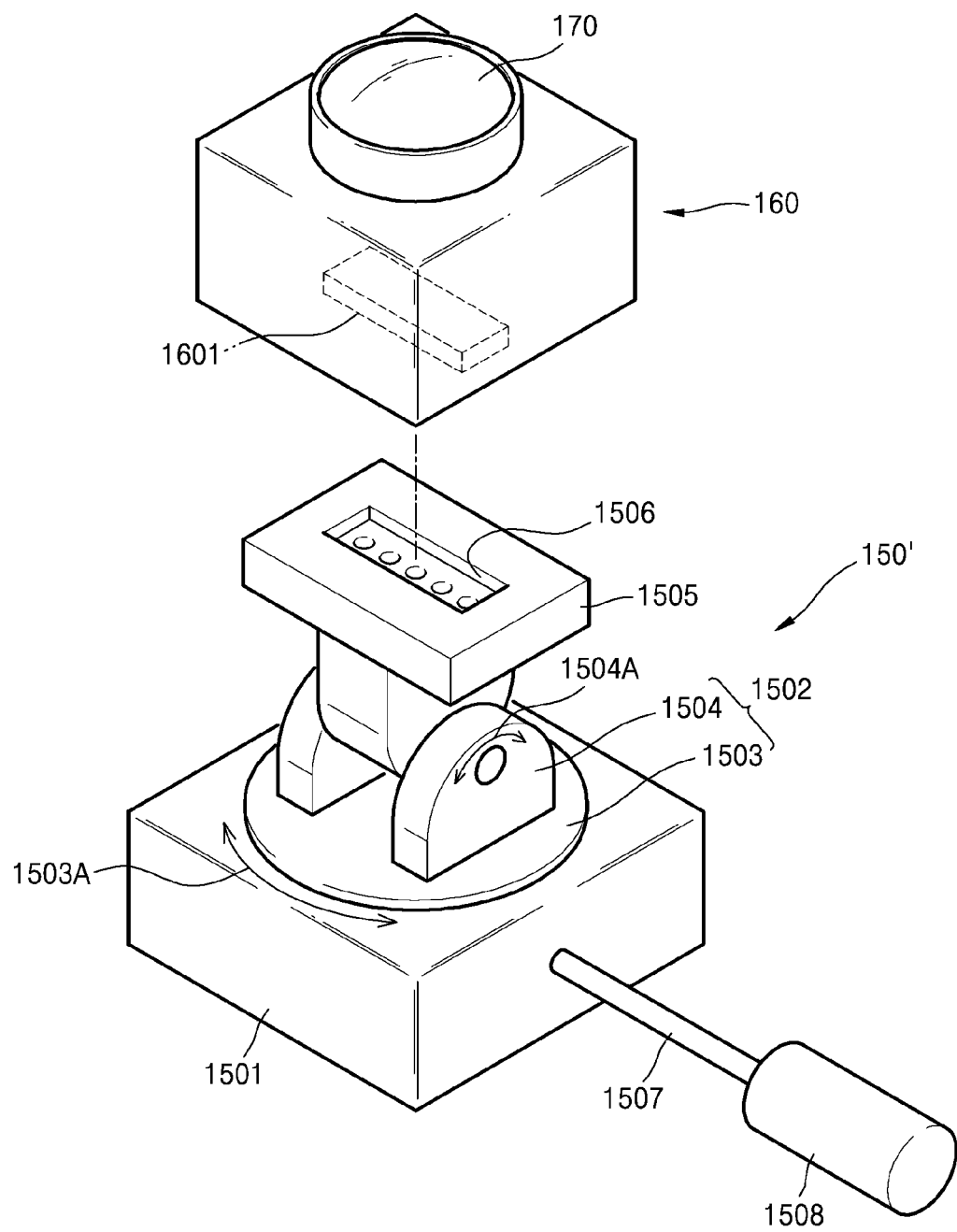
FIG. 11 illustrates a schematic configuration of a detachable module applied to the MRI apparatus of FIG. 10.

FIG. 10 illustrates a schematic configuration of an MRI apparatus 100' according to another exemplary embodiment. FIG. 11 illustrates a schematic configuration of a detachable module 150' applied to the MRI apparatus 100' of FIG. 10. Except the detachable module 150', the MRI apparatus 100' according to the present exemplary embodiment substantially includes the same elements as those of the MRI apparatus 100 described above and repeated descriptions are omitted.

Referring to FIGS. 10 and 11, the detachable module 150' according to the present exemplary embodiment may include first and second detachable modules 150'-1 and 150'-2 that are respectively disposed at positions adjacent to both ends in a length direction of the moving table 121. The first and second detachable modules 150'-1 and 150'-2 may include the same elements. In the following description, the detachable module 150' may refer to one of the first and second detachable modules 150'-1 and 150'-2.

The detachable module 150' may include a base material 1501, which is fixed onto the moving table 121, and a rotation unit 1502 that is provided at the base material 1501. The rotation unit 1502 may include, for example, a first rotation unit 1503 that rotates in one of first directions as indicated by a reference numeral 1503A and a second rotation unit 1504 that rotates in one of second directions as indicated by a reference numeral 1504A. The first and second directions 1503A and 1504A may be different directions, and thus, a rest 1505 may face an arbitrary direction by a combination of the first and second directions 1503A and 1504A. For example, the first direction 1503A of the first rotation unit 1503 may be a rotation direction which has a normal-line direction of the base material 1501 as a rotation axis, and the second direction 1504A may be a rotation direction which has, as a rotation axis, a direction vertical to the rotation axis of the first direction 1503A.

The detachable module 150' may further include a driving motor 1508 that rotates the rotation unit 1502. The driving motor 1508 is controlled by the MRI controller 180. A driving shaft 1507, which transfers driving force between the rotation unit 1502 and the driving motor 1508, may be hard or flexible. When the rotation unit 1502 is configured with the first and second rotation units 1503 and 1504, the driving force transferred through the driving shaft 1507 may be selectively distributed to the first and second rotation units 1503 and 1504. The driving motor 1508 may be disposed outside the housing 110 without entering the bore of the housing 110, and may provide the driving force to the rotation unit 1502 through the driving shaft 1507. When the driving motor 1508 is disposed outside the housing 110, despite an electromagnetic motor being used as the driving motor 1508, an interaction with the internal magnetic field of the bore of the housing 110 is minimized, thereby reducing a burden of the electromagnetic shield.

The rest 1505, in which the beam projector 160 is detachably provided, is provided at the rotation unit 1502. A connector 1506, which establishes an electrical and mechanical connection with the connector 1601 of the beam projector 160, is provided at the rest 1505. A plurality of electrode terminals, which transfer the video signal and the control signal from the MRI controller 180 to the beam projector 160, are provided at the connector 1506 of the rest 1505. The video signal, the control signal, and power may be transferred from the detachable module 150' to the beam projector 160 through a mutual connection between the connector 1506 of the detachable module 150' and a connector terminal 1601 of the beam projector 160.

Rotation of the rotation unit 1502 changes a direction of the rest 1505 with the beam projector 160 mounted thereon, and thus, an image projection direction of the beam projector 160 may be changed to correspond to a looking direction of the an object.

A motor driver (not shown) for driving the driving motor 1506 may be additionally provided at the detachable module 150'. The motor driver may receive motor power and a control signal, which are used to drive the driving motor 1506, from the MRI controller 180 to drive the driving motor 1506, thereby changing the image projection direction of the beam projector 160.

Figure 12:
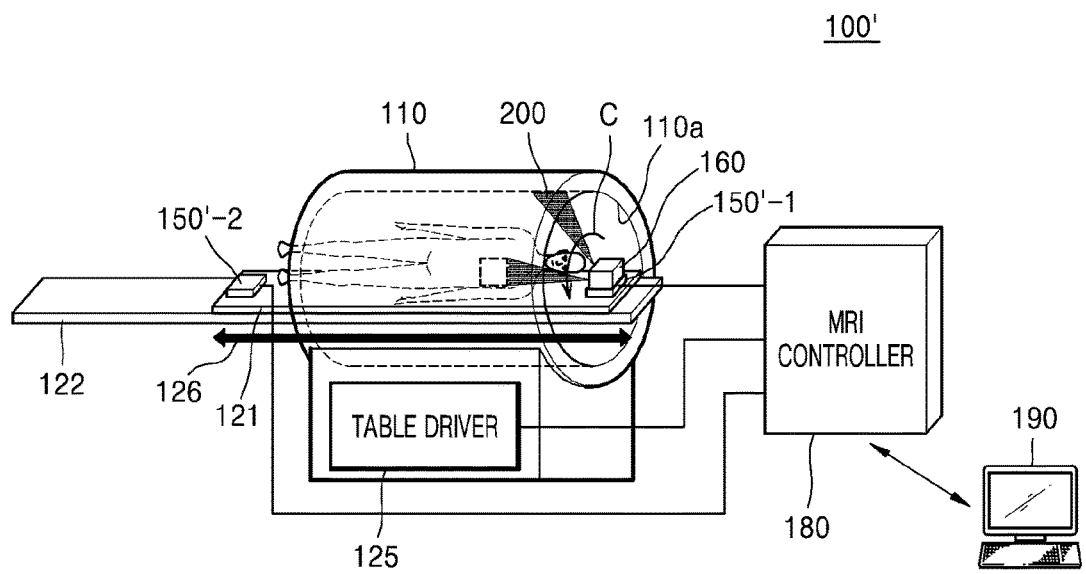
FIG. 12 illustrates an operation of the MRI apparatus of FIG. 10.

FIG. 12 illustrates an operation of the MRI apparatus 100' of FIG. 10.

A direction, in which an object lies on the moving table 120, may be changed according to an imaging purpose. For example, as illustrated in FIG. 12, the object may lie on its side for the purpose of capturing an image. In this case, eyes of the object face a side direction, and thus, the detachable module 150' (the first detachable modules 150'-1 or the second detachable modules 150'-2 in FIG. 11) with the beam projector 160 mounted thereon may rotate (arrow C) the rotation unit 1502 in order for the image projection direction of the beam projector 160 to face the side direction substantially coinciding with a looking direction of the object.

The image projection direction of the beam projector 160 may be changed automatically or by manual manipulation of a user. For example, when the object lies on its side, the user may manipulate the console 190 in order for the image projection direction of the beam projector 160 to face the side direction, in response to a movement of the object.

The MRI apparatus 100' may further include a position tracing sensor 140, as shown in FIG. 10, that detects a lying position of the object or a direction which eyes of the object face. The position tracing sensor 140 may be a camera, which photographs a face of the object, or the other known sensor. For example, when the position tracing sensor 140 is the camera, a face photograph of the object is transferred to the MRI controller 180, and a signal processor 185 of the MRI controller 180 detects an eyeball position of the object from the face photograph of the object. A method, which detects the eyeball position from the face photograph, is known to those skilled in the art, and thus, its detailed description is not provided. The MRI controller 180 may automatically rotate (arrow C) the rotation unit 1502 of the detachable module 150' in order for the image projection direction of the beam projector 160 to face a direction substantially coinciding with the looking direction of the object, in response to the detected eyeball position of the object.

An exemplary embodiment described above with reference to FIGS. 10 to 12, the rotation unit 1502 provided at the detachable module 150' is an example of a projection direction changing unit that changes a projection direction of the beam projector 160. As another example, the projection direction changing unit may be provided at the beam projector itself. For example, the projection lens 170 may be mounted on a housing of the beam projector 160 so as to enable a direction of the projection lens 170 to be changed.

Moreover, in an exemplary embodiment described above with reference to FIGS. 10 to 12, a driving module configured with the driving shaft 1507 and the driving motor 1508 is described as an example, but the other known driving scheme may be applied. For example, a hydraulic system may be applied as the driving module for the rotation unit 1502 of the detachable module 150'. Furthermore, the rotation unit 1502 may be manually rotated.

Moreover, in an exemplary embodiment described above with reference to FIGS. 10 to 12, a configuration in which the first and second rotation units 1503 and 1504 of the detachable module 150' change a direction of the rest 1505 through a combination of lateral rotation and vertical rotation is described as an example, but single-axis rotation or multi-axis rotation may be applied to the rotation unit of the detachable module 150'. Furthermore, a coupling position in which the beam projector 160 is coupled or docked to the detachable module 150' may be provided as a plurality of positions including an upper side, a left side, and a right side of the detachable module 150', and thus, the image projection direction of the beam projector 160 may be changed by selectively changing the position in which the beam projector 160 is coupled to the detachable module 150'.

An image projected onto the inner wall 110*a* may be distorted due to a curved shape of the inner wall 110*a*, especially when the image projection is moved along a circumference of the inner wall 110*a*. Also, an optical beam may be projected askew with respect to the inner wall 110*a* due to gradient projection and an amount of a skew distortion may vary when the image projection direction is moved in a vertical direction of the housing 110. Therefore, the beam projection controller 165 or the MRI controller 180 causes a primary pre-distortion which counteracts the curved-surface distortion or the skew distortion in an image signal processing operation, thereby removing the curved-surface distortion of an image formed on the curved inner wall 110*a*.

In the above-described exemplary embodiments, the first and second detachable modules 150-1 and 150-2 (or 150'-1 and 150'-2) are described as an example, but a number of the detachable modules of an exemplary embodiment is not limited thereto. For example, a number of the detachable modules may be one, three, etc., and the detachable modules may be provided at one, three or more positions on the moving table 121. Furthermore, the beam projector 160 may be fixed to and disposed on the moving table 121 without using any of the detachable modules.

Moreover, in the above-described exemplary embodiments, the bore is described to be cylindrical, as an example, but an exemplary embodiment is not limited thereto. For example, the bore of the housing 110 may have an oval shape, or have the other shape.

Figure 13:
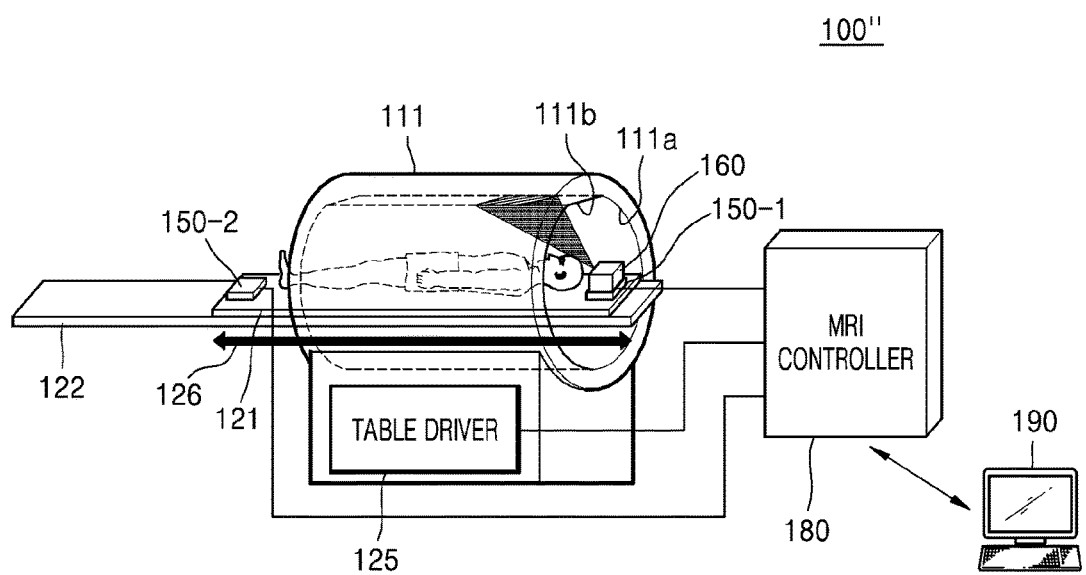
FIG. 13 illustrates a schematic configuration of an MRI apparatus according to another exemplary embodiment.

FIG. 13 illustrates a schematic configuration of an MRI apparatus 100" according to another exemplary embodiment. Referring to FIG. 13, a bore of a housing 111 of the MRI apparatus 100" may include a curved inner wall 111*a* and a planar inner wall 111*b*. The planar inner wall 111*b* may be disposed on the bore of the housing 111. The planar inner wall 111*b* may be formed to extend in a length direction of the bore of the housing 111. Except a structure of the bore of the housing 111, the MRI apparatus 100" according to the present exemplary embodiment substantially includes the same elements as those of the MRI apparatuses 100 and 100' described above and repeated descriptions are omitted.

The beam projector 160 may project an image onto the planar inner wall 111*b*. A flat plate may be disposed at an upper portion corresponding to a direction in which eyes of an object face in a state of lying supinely on the moving table 121. The object may look at the image projected by the beam projector 160 in a state of lying supinely on the moving table 121. When the image is projected onto the planar inner wall 111*b*, curved-surface distortion does not occur in the projected image, and thus, correction for the curved-surface distortion may be omitted from the signal processing operation described above.

In the present exemplary embodiment, a case in which the planar inner wall 111*b* is disposed in the top of the bore of the housing 111 is described as an example, but an exemplary embodiment is not limited thereto. For example, the planar inner wall 111*b* may be disposed at a side of the bore of the housing 111.

Furthermore, in the present exemplary embodiment, a case in which only one planar inner wall 111*b* is provided is described as an example, but an exemplary embodiment is not limited thereto. That is, the bore of the housing 111 may be configured by a combination of a plurality of planar inner walls and a curved inner wall, or may be configured with only the plurality of planar inner walls. For example, all inner walls configuring the bore of the housing 111 may be planar inner walls, and a horizontal cross-sectional surface of the bore may have a polygonal shape.

As described above, in the MRI apparatus according to the exemplary embodiments, since the beam projector is disposed in the bore, various contents are provided to an object being imaged. In addition, the coil of the beam projector is disposed in consideration of a direction of a magnetic field, and thus, even when the light source driver using an inductor having a coil structure is applied, occurrence of noise is prevented, thereby enabling an MR image of an object to be captured in a comfortable state.

The foregoing exemplary embodiments and advantages are merely exemplary and are not to be construed as limiting. The exemplary embodiments can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A magnetic resonance imaging (MRI) apparatus comprising:
    a housing that includes a bore;
    a table which is configured to be moved into the bore; and
    a beam projector that is configured to be disposed on the table, and to project an image into the bore,
    wherein the beam projector includes a coil, and
    the coil is configured to be disposed so that a central axis of the coil is parallel to a center axis of the bore.

2. The MRI apparatus of claim 1, wherein the coil comprises an air-core coil.

3. The MRI apparatus of claim 1, wherein the coil is a cylindrical coil.

4. The MRI apparatus of claim 1, wherein the coil is a cylindrical air-core coil.

5. The MRI apparatus of claim 1, wherein the beam projector comprises:

an image panel configured to display the image;
a light source configured to emit light onto the image panel;
a light source driver configured to supply a power to the light source; and
a projection lens configured to project the image displayed by the image panel,
wherein the coil comprises an inductor provided at the light source driver.

6. The MRI apparatus of claim 5, wherein the light source driver comprises a DC converter that converts an input DC voltage into a DC voltage of at least one another level.

7. The MRI apparatus of claim 5, wherein the light source comprises red, green, and blue (RGB) light sources, and
the light source driver sequentially supplies a current to the RGB light sources.

8. The MRI apparatus of claim 1, wherein an image-forming position, in which the image projected from the beam projector is formed inside the bore of the housing, is moved according to a position to which the table is moved in the bore.

9. The MRI apparatus of claim 1, wherein the beam projector is disposed near at least one of a first end and a second end of the table, in a length direction of the table.

10. The MRI apparatus of claim 1, further comprising a detachable module configured to be disposed on the table and to be detachably attached to the beam projector.

11. The MRI apparatus of claim 1, wherein the beam projector comprises a luminance sensor configured to detect a brightness level inside the bore, and
the MRI apparatus further comprises a controller configured to control a beam brightness of the beam projector according to the detected brightness level in the bore.

12. The MRI apparatus of claim 1, wherein the projected image comprises at least one of an MR image being captured, an MR imaging information, and a video content.

13. The MRI apparatus of claim 1, further comprising a controller configured to control the beam projector, and transfer a video signal to the beam projector.

14. A method of displaying an image in a bore of a magnetic resonance imaging (MRI) apparatus, the method comprising:
disposing a beam projector on a table which is movable;
moving the table into a bore of a housing of the MRI apparatus; and
projecting an image into the bore by the beam projector,
wherein the beam projector includes a coil, and
the coil is configured to be disposed so that a central axis of the coil is parallel to a center axis of the bore.

15. The method of claim 14, wherein the coil is an air-core coil.

16. The method of claim 14, wherein the coil is a cylindrical coil.

17. The method of claim 14, wherein the coil is a cylindrical air-core coil.

18. The method of claim 14, wherein the beam projector comprises:
an image panel configured to display the image;
a light source configured to emit light onto the image panel;
a light source driver configured to supply a power to the light source; and
a projection lens configured to project the image displayed by the image panel,
wherein the coil comprises an inductor provided at the light source driver.

19. The method of claim 14, wherein an image-forming position, in which the image projected from the beam projector is formed inside the bore of the housing, is moved according to a position to which the table moves in the bore.

20. The method of claim 14, wherein the beam projector is disposed in the bore when the table enters an inside of the bore.

21. The method of claim 14, wherein the projected image comprises at least one of an MR image being captured, an MR imaging information, and a video content.

* * * * *